(12) United States Patent
Murphy et al.

(10) Patent No.: US 9,566,015 B2
(45) Date of Patent: Feb. 14, 2017

(54) NERVE MONITORING DURING ELECTROSURGERY

(71) Applicant: MEDTRONIC XOMED, INC., Jacksonville, FL (US)

(72) Inventors: John Murdock Murphy, Jacksonville, FL (US); John A. Meyer, Hilton Head Island, SC (US); Adnorin Luis Mendez, Jacksonville, FL (US); Kevin Lee McFarlin, Jacksonville, FL (US); David C. Hacker, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 88 days.

(21) Appl. No.: 14/626,127

(22) Filed: Feb. 19, 2015

(65) Prior Publication Data

US 2015/0157237 A1  Jun. 11, 2015

Related U.S. Application Data

(62) Division of application No. 12/363,154, filed on Jan. 30, 2009, now Pat. No. 8,989,855.

(51) Int. Cl.
*A61B 5/0488* (2006.01)
*A61B 5/04* (2006.01)
(Continued)

(52) U.S. Cl.
CPC ......... *A61B 5/0488* (2013.01); *A61B 5/04012* (2013.01); *A61B 5/7217* (2013.01); *A61B 5/7264* (2013.01); *A61B 17/32* (2013.01)

(58) Field of Classification Search
CPC .............. A61B 5/0488; A61B 5/04001; A61B 5/04004; A61B 5/4893; A61B 18/1402; A61B 6/506; A61B 19/56; A61B 2017/00119; A61B 2017/00022–2017/00053; A61B 2018/00839
See application file for complete search history.

(56) References Cited

U.S. PATENT DOCUMENTS 4,934,377 A   6/1990   Bova et al.
6,181,961 B1  1/2001   Prass
(Continued)

FOREIGN PATENT DOCUMENTS

CN    1401294 A     3/2003
JP    2000-316855 A  11/2000
(Continued)

OTHER PUBLICATIONS

PCT Preliminary Report and Written Opinion mailed Aug. 2, 2011, 7 pages.

*Primary Examiner* — Adam J Eiseman
(74) *Attorney, Agent, or Firm* — Dicke, Billig & Czaja, PLLC

(57) ABSTRACT

A signal processing module includes an input module electronically coupled to a sensing probe of a nerve integrity monitoring system. The probe senses electrical signals from a patient during operation of an electrosurgical unit. The input module receives an input signal from the probe. An EMG detection module is coupled to the input module and is adapted to detect conditions in the input signal. The conditions are classified as a function of a level of electromyographic activity. An output module, coupled to the EMG detection module, provides an indication of electromyographic activity in the input signal based on the detected conditions.

12 Claims, 7 Drawing Sheets

(51) Int. Cl.
*A61B 5/00* (2006.01)
*A61B 17/32* (2006.01)

(56) References Cited

U.S. PATENT DOCUMENTS

| | | |
|---|---|---|
| 6,334,068 B1 | 12/2001 | Hacker |
| 6,370,412 B1 | 4/2002 | Armoundas et al. |
| 6,547,746 B1 * | 4/2003 | Marino ............... A61B 5/04 600/544 |
| 7,310,546 B2 | 12/2007 | Prass |
| 2006/0155270 A1 | 7/2006 | Hancock et al. |
| 2009/0018429 A1 * | 1/2009 | Saliga et al. ............... 600/407 |
| 2010/0145221 A1 * | 6/2010 | Brunnett et al. ............ 600/554 |
| 2010/0145222 A1 * | 6/2010 | Brunnett et al. ............ 600/554 |

FOREIGN PATENT DOCUMENTS

| | | |
|---|---|---|
| WO | 03/037170 A2 | 5/2003 |
| WO | 2008097407 A2 | 8/2008 |

\* cited by examiner

NERVE MONITORING DURING ELECTROSURGERY

CROSS-REFERENCE TO RELATED APPLICATIONS

This application is a Divisional Application of U.S. patent application Ser. No. 12/363,154 having a filing date of Jan. 30, 2009, and which is incorporated herein by reference.

BACKGROUND

The present disclosure relates to a nerve monitoring system. More particularly, it relates to monitoring nerve activity during electrosurgery or in the presence of electrical artifacts from metal surgical instruments.

Electrophysiological monitoring assists a surgeon in locating nerves within an obscured surgical field, as well as preserving and assessing nerve function in real-time during surgery. To this end, nerve integrity monitoring is commonly employed to monitor electromyographic (EMG) activity. During nerve integrity monitoring, sensing or recording electrodes are coupled to appropriate tissue (e.g., cranial muscles innervated or controlled by the nerve of interest, peripheral nerve, spinal cord, brainstem, etc.) to sense EMG activity. Stimulation, for example electrical stimulation or mechanical stimulation, can cause excitement of the tissue. During electrical stimulation, a stimulation probe applies a stimulation signal near the area where the subject nerve may be located. If the stimulation probe contacts or is reasonably near the nerve, the applied stimulation signal is transmitted through the nerve to excite the innervated tissue. In mechanical stimulation, direct physical contact of the appropriate tissue can cause excitement of the tissue. In any event, excitement of the related tissue generates an electrical impulse that is sensed by the recording electrodes (or other sensing device). The recording electrode(s) signal the sensed electrical impulse information to the surgeon for interpretation in the context of determining EMG activity. For example, the EMG activity can be displayed on a monitor and/or presented audibly.

Nerve integrity monitoring is useful for a multitude of different surgical procedures or evaluations that involve or relate to nerve tissue, muscle tissue, or recording of neurogenic potential. For example, various head and neck surgical procedures require locating and identifying cranial and peripheral motor nerves. In some instances, an electrosurgical unit is used to perform these surgical procedures. Current electrosurgical units include a conductive tip or needle that serves as one electrode in an electrical circuit which is completed via a grounding electrode coupled to the patient. Incision of tissue is accomplished by applying a source of electrical energy (most commonly, a radio-frequency generator to the tip). Upon application of the tip to the tissue, a voltage gradient is created, thereby inducing current flow and related heat generation at the point of contact. With sufficiently high levels of electrical energy, the heat generated is sufficient to cut the tissue and, advantageously, to simultaneously cauterize severed blood vessels.

Due to the levels of electrical energy generated by electrosurgical units, systems for nerve integrity monitoring experience a large amount of electrical interference when used during electrosurgical procedures. The electrical interference can create incorrect signals of EMG activity (e.g., false positives) as well as introduce a significant amount of noise in the nerve integrity monitoring system. As a result, current techniques involve using a probe to mute all channels of the nerve integrity monitoring system during an electrosurgical procedure. As a result, monitoring of EMG activity is suspended during operation of the electrosurgical unit. In order for a surgeon to prevent cutting a nerve with the electrosurgical unit, the surgeon will cut for a brief period and then stop cutting such that nerve integrity monitoring can be restored. If no EMG activity is detected, the surgeon can then cut for another brief period, while pausing intermittently to restore nerve integrity monitoring so as to prevent from cutting a nerve. This process is repeated until the surgeon is completed with the electrosurgical procedure. Without being able to monitor EMG activity during an electrosurgical procedure, the electrosurgical procedure can be cumbersome and time consuming.

SUMMARY

Concepts presented herein relate to a signal processing module, a surgical method and a nerve integrity monitoring system. An input module of the signal processing module is electronically coupled to a sensing probe of the nerve integrity monitoring system. The probe senses electrical signals from a patient during operation of an electrosurgical unit. The input module receives an input signal from the probe. An EMG detection module is coupled to the input module and is adapted to detect conditions in the input signal. The conditions are classified as a function of a level of electromyographic activity. An output module, coupled to the EMG detection module, provides an indication of the detected conditions.

An artifact detection module can also be employed to detect an artifact condition in the input signal. The artifact detection module can estimate a power of the input signal to detect the artifact. Additionally, other modules can be included such as a direct current filter module and an EMG recovery module.

DETAILED DESCRIPTION

Figure 1:
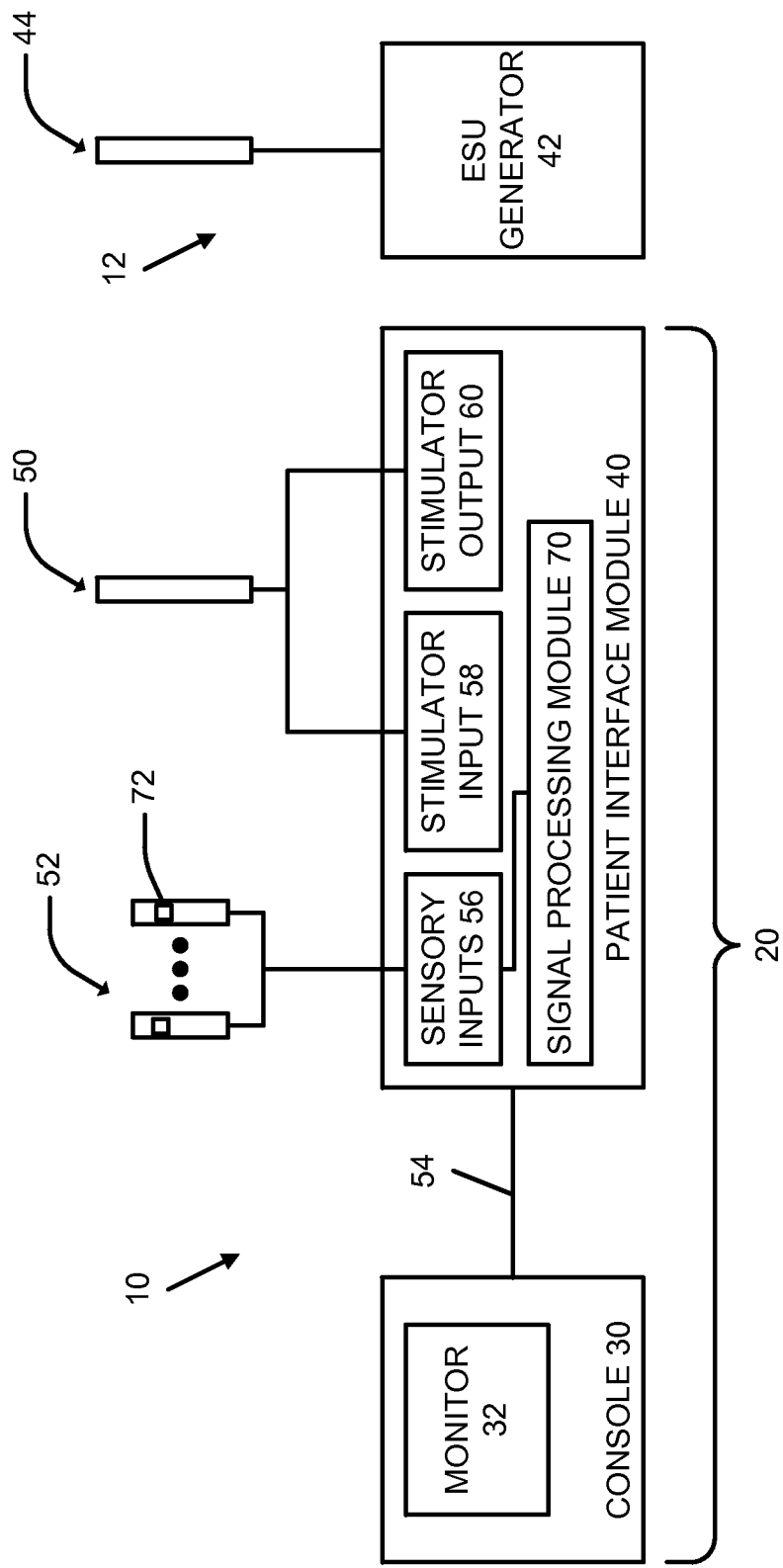
FIG. 1 is a schematic block diagram of a surgical environment including a nerve integrity monitoring system and an electrosurgical unit.

A surgical environment including a nerve integrity monitoring system 10 and an electrosurgical unit (ESU) 12 is illustrated in FIG. 1. In general terms, the system 10 is configured to assist in and perform nerve integrity monitoring for virtually any nerve/muscle combination of the human anatomy, as well as recording nerve potential. The system 10 includes a control unit 20, which can assume a wide variety of forms and in one embodiment includes a console 30, having a monitor 32, and a patient interface module 40. The electrosurgical unit 12 includes an ESU generator 42 coupled to a surgical instrument 44. The ESU generator 42 generates current that is sent to surgical instrument 44 for cutting or otherwise manipulating tissue of a patient.

System 10 includes a stimulation probe assembly 50, which can be used for electrical stimulation, as well as one or more sensing probes 52, which can be any type of sensing device such as an electrode. The control unit 20 facilitates operation of the probe assembly 50, as well as processes all information generated by sensing probes 52 and other system 10 components (not shown) during use. The probe assembly 50 and the control unit 20 are adapted to allow control and variation of a stimulus energy delivered to, and thus a stimulus level delivered by, the probe assembly 50 via an actuator provided on the probe assembly 50 (remote of the control unit 20). To this end, the probe assembly 50 and the control unit 20 are adapted to allow continuous variation (e.g., increment or decrement) of the stimulation energy over a series of discrete, sequential steps via manipulation of the probe assembly 50 actuator. Further, the control unit 20 processes information (e.g., patient response) received from sensing probes 52 resulting from delivered stimulation.

Using the sensing probes 52, the system 10 performs monitoring based upon recorded EMG activity in response to an electrical current energy delivered by the probe assembly 50 and/or physical manipulation of tissue. With the one embodiment of FIG. 1, the console 30 and the patient interface module 40 are provided as separate components, communicatively coupled by a cable 54. Alternatively, a wireless link can be employed. Further, the console 30 and the patient interface module 40 can be provided as a single device. In basic terms, however, the patient interface module 40 serves to promote easy connection of stimulus/sensory components (such as the probe assembly 50 and sensing probes 52), as well as to manage incoming and outgoing electrical signals. The console 30, in turn, interprets incoming signals (e.g., impulses sensed by sensing probes 52), displays information desired by a user, provides audible feedback of signals, presents a user interface (such as by including, for example, a touch screen), and delivers a stimulation energy to the probe assembly 50 pursuant to control signals from the probe assembly 50 (via connection to the patient interface module 40), as well as other tasks as desired.

As previously described, the patient interface module 40 communicates with the console 30 through the cable 54 information to and from the probe assembly 50, as well as information from the sensing probes 52. In effect, the patient interface module 40 serves to connect the patient (not shown) to the console 30. To this end, and in one embodiment, the patient interface module 40 includes one or more (preferably eight) sensory inputs 56, such as pairs of electrode inputs electrically coupled to receive signals from the sensing probes 52 (referenced generally in FIG. 1). In addition, the patient interface module 40 provides a stimulator input port 58 (referenced generally in FIG. 1) and a stimulator output port 60 (referenced generally in FIG. 1). The stimulator input port 58 receives control signals from the probe assembly 50 relating to desired stimulation levels and/or other activities, whereas the stimulator output port 60 facilitates delivery of stimulation energy to the probe assembly 50. The patient interface module 40 can further provide additional component port(s), such as a ground (or return electrode) jack, auxiliary ports for additional stimulator probe assemblies, etc.

The control unit 20, and in particular the console 30 and the patient interface module 40, are akin in several respects to available monitoring systems, such as the NIM-Response™ Nerve Integrity Monitor, available from Medtronic Xomed of Jacksonville, Fla. For example, the touch screen capabilities provided by the NIM-Response™ Nerve Integrity Monitor can be incorporated into the control unit 20. In addition, however, the system 10 employs a signal processing module 70, which performs signal processing techniques that classifies input signals received from sensing probes 52 and delivers an output signal regarding nerve monitoring during operation of electrosurgical unit 12. In particular, the signal processing module 70 can provide an indication of low EMG activity (including no EMG activity) or high EMG activity during operation of the electrosurgical unit 12. Additionally, the signal processing module 70 can selectively mute one or more channels of information provided from the sensing probes 52 to the sensory input ports 56, block a direct current (DC) component or low frequency noise in signals received and recover EMG data.

The sensing probes 52 are coupled to the patient (e.g., selected tissue) to provide signals to the signal processing module 70. In one embodiment, the plurality of probes 52 includes eight probes that are electronically coupled to sensory inputs 56. In normal operation, the probes 52 sense electrical signals from the patient and send the signals to signal processing module 70. These signals include an electrical impulse from patient tissue, which is indicative of EMG activity in the patient. However, several conditions can introduce noise into probes 52 and thus corrupt signals provided to the signal processing module 70. For example, the current generated by ESU 12 creates noise that is detected by one or more of the probes 52.

Each of the plurality of probes 52 constitutes a separate channel that can be independently processed in signal processing module 70, as discussed below. For example, if a total of eight sensing probes are used, eight separate channels can be independently processed by signal processing module 70. To this end, the signal processing module 70 includes components that classify signals received from the sensing probes 52 and allows a surgeon to maintain monitoring of nerve activity for one or more channels during an electrosurgical procedure. The classification can be a low level of EMG activity (including zero) or a high level of EMG activity.

In one embodiment, each of the plurality of probes 52 includes a front-end filter, for example filter 72, that can be utilized to filter the fundamental frequency generated by the ESU 12. Alternatively, a single front-end filter can be provided to filter the signals received from each of the sensing plurality of probes 52. Through analysis of operation of ESU 12 and/or signals generated by ESU 12, it can be determined what components are present during operation of the ESU 12. In one embodiment, the ESU 12 generates a 29 kHz pulsed 500 kHz radiofrequency signal as well as additional harmonics. Filter 72 can be adjusted so as to optimize filtering of the signal generated by ESU 12 and thus reduce noise provided to signal processing module 70.

Figure 2:
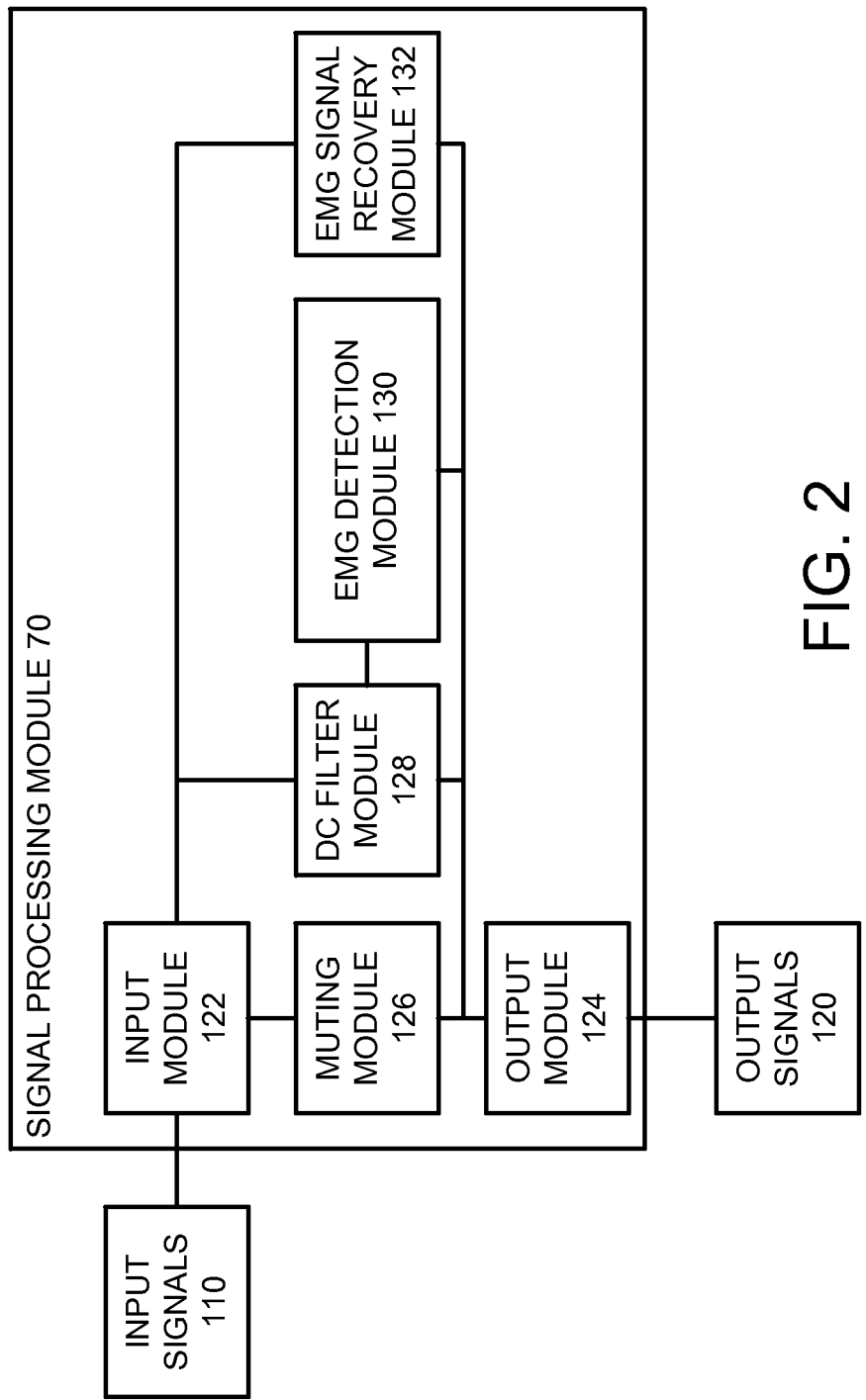
FIG. 2 is a schematic block diagram of a signal processing module in the nerve integrity monitoring system of FIG. 1.

FIG. 2 is a schematic block diagram of signal processing module 70, which receives input signals 110 and processes the signals to produce output signals 120 indicative of a level of EMG activity in the input signals 110. The output signals 120 can further be supplemented by additional indications, for example an artifact detection condition, a recovered EMG signal, etc. Signals from the sensing probes 52 (FIG. 1) are received in signal processing module 70 through an input module 122. Illustratively, input module 122 can associate signals with a particular probe (i.e., channel) that is used by other modules within signal processing module 70. In addition, input module 122 can include an analog-to-digital convert (ADC), which samples the signals received at a specified rate in order to convert the signals from an analog form to a digital form, as discussed in more detail below. In addition to input module 122, signal processing module 70 includes an output module 124 that provides the output signals 120, for example to console 30 (FIG. 1). Between input module 122 and output 124 are a plurality of modules for detecting conditions in signals received by the input module 122 and providing a corresponding response to output module 124 such that nerve integrity monitoring can be maintained during an electrosurgical procedure. In particular, signal processing module 70 includes an artifact detection module 126, a DC filter module 128, an EMG detection module 130 and an EMG signal recovery module 132.

Figure 3:
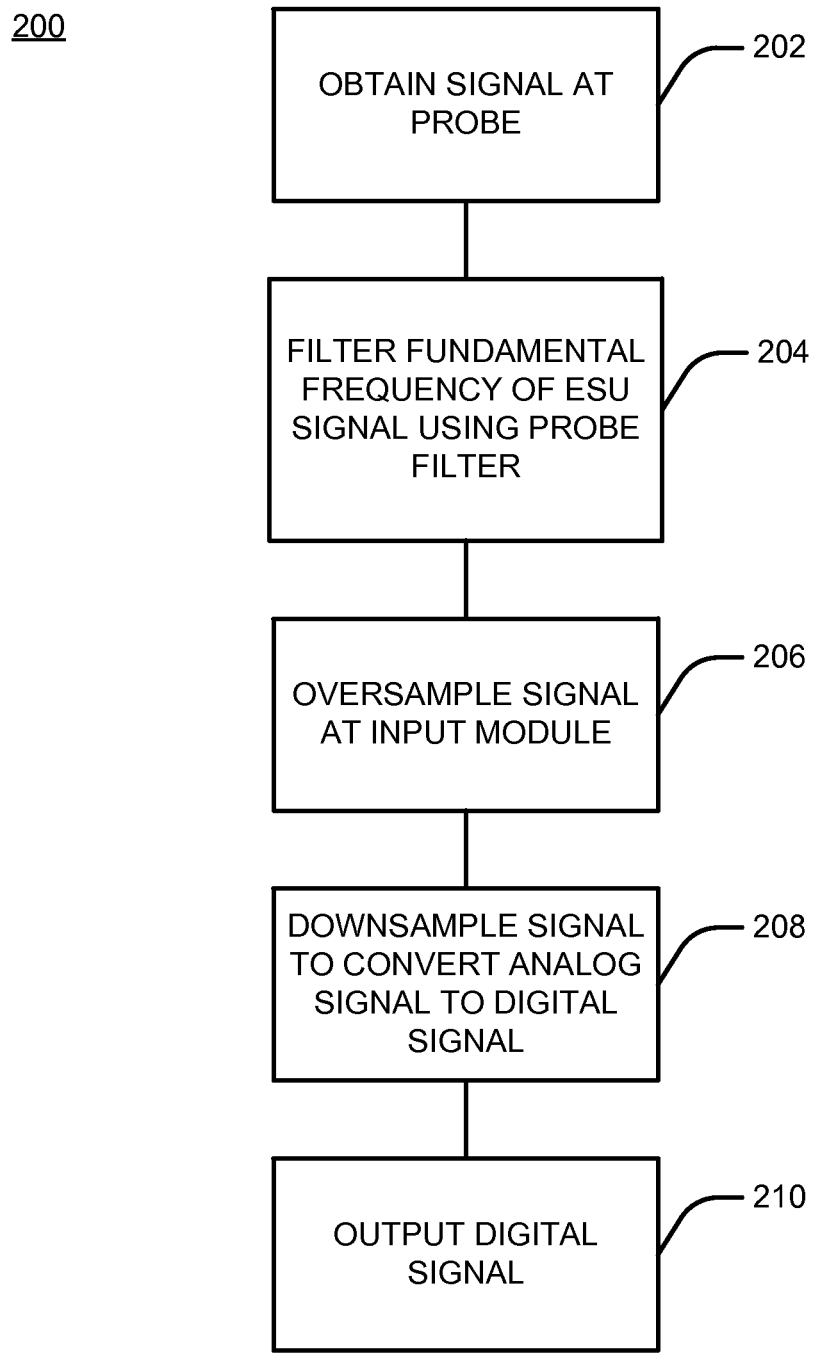
FIG. 3 is a flow diagram of a method for processing signals in the nerve integrity monitoring system of FIG. 1.

FIG. 3 is a flow diagram of a method 200 for front-end processing of signals obtained by nerve integrity monitoring system 10 and in particular sensing probes 52. At step 202, a signal is obtained by a sensing probe, for example one or more of probes 52. The signal is indicative of both ESU data (as caused by operation of ESU 12) as well as EMG activity (as caused by nerve potential from the patient). At step 204, the fundamental frequency of ESU data is filtered. This filtering can be performed by filter 72 at probe 52 (FIG. 1), for example. The filtered signal is then sent to input module 122 of signal processing module 70.

As discussed above, the input module 122 includes an ADC operating at a sampling rate to process signals received from the sensing probes 52. To prevent aliasing, the input module 122, at step 206, oversamples the signal from probes 52. Since electrosurgical unit 12 generates noise having a wide range of frequencies, oversampling can be used to prevent aliasing in the signal received. The oversampling rate can be several times greater than a sampling rate of the ADC. In one embodiment, the oversampling rate can be 128 times the sampling rate. At step 208, the signal can be downsampled using a decimation filter to convert the analog signal sensed at the probes 52 to a digital signal. The digital signal is output at step 210. In one example, the ADC samples the signal at a rate of 16 kHz. If the signal is oversampled in step 206 at a rate of 128 times the sampling rate, or 2.048 MHz aliasing can be prevented in component frequencies less than 1.024 MHz and ESU signals greater than 8 kHz should not be present in the digital signal output at step 210. The digital signal can be sent to artifact detection module 126, DC filter module 128, EMG detection module 130 and/or EMG signal recovery module 132. As discussed below, these modules can process the digital signal to detect conditions that are provided to output module 124.

Figure 4:
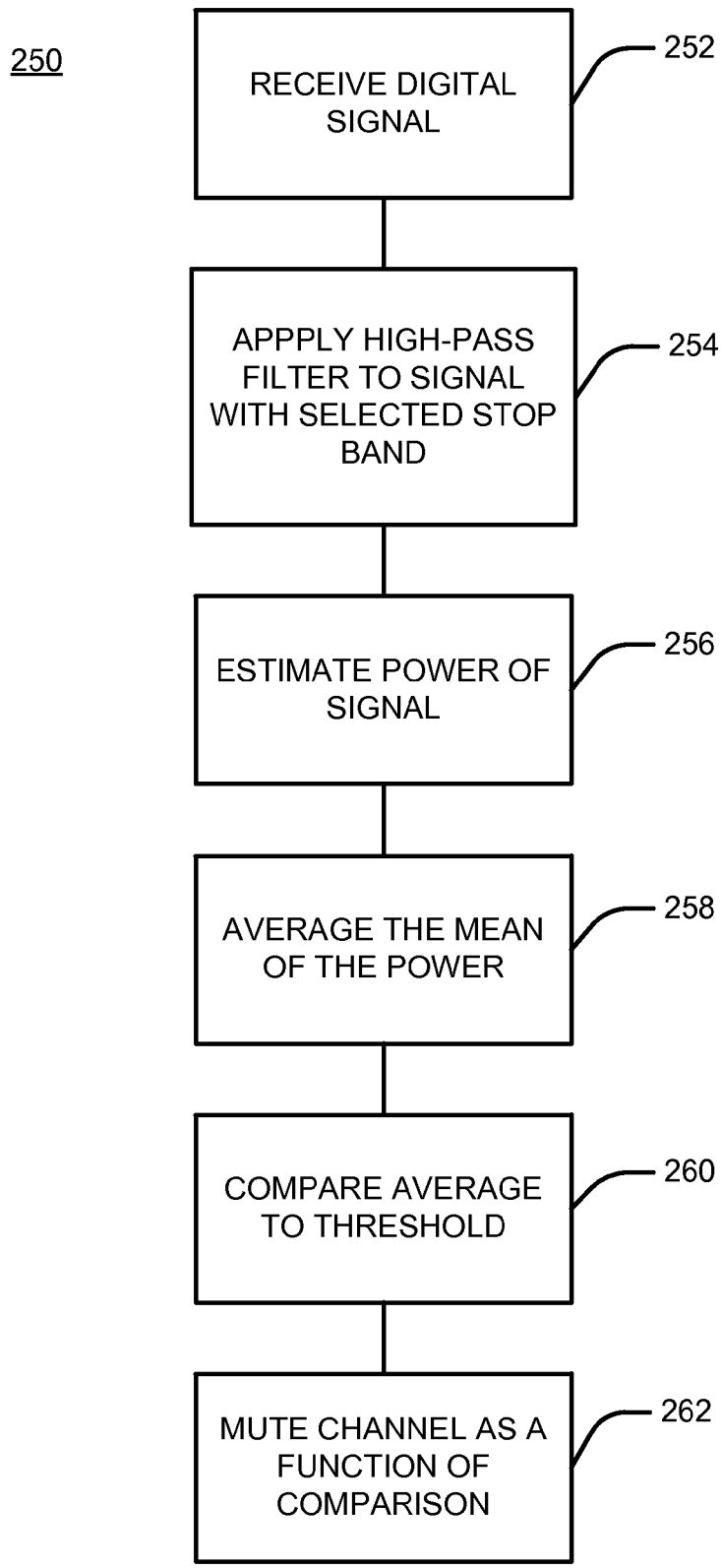
FIG. 4 is a flow diagram of a method for detecting an artifact in one or more channels that provide input to the nerve integrity monitoring system of FIG. 1.

FIG. 4 is a flow diagram of a method 250 for detecting an artifact in one or more channels provided to signal processing module 70, as performed by artifact detection module 126. The artifact detection module 126 can aid in situations for detecting artifacts that can be caused be metal surgical instruments contacting tissue and/or situations where two or more surgical instruments contact each other.

The metal-to-metal (or metal to patient) artifact can be produced when instruments with different static electrical charge contact each other or the patient causing a current to flow as the charge is equalized. The charge transfer is by a spark which contains broad band noise spectrum including high frequency far above EMG. The night frequency shows up on the monitor as a fast vertical response not possible to be EMG. This often is on multiple channels at the same time needing filtering.

If a signal for a channel is likely an artifact, the channel can be muted independent of other channels so as to prevent an indication of a false positive of EMG activity. At step 252, the digital signal generated by method 200 (FIG. 3) is received into artifact detection module 126 from input module 122. At step 254, a high pass filter is applied to the digital signal with a stop band having a range that excludes EMG data. In one example, EMG activity is determined to be in a range from 0 to 3.5 kHz and thus the stop band applied is from 0 to 3.5 kHz. The resulting signal is a band limited signal that can further be processed to determine if the channel associated with the signal should be muted.

At step 256, the power of the band limited signal is estimated by squaring the signal and finding a mean over a sample buffer. The buffer can be any size and in one example includes 80 samples, constituting 5 milliseconds of data. The mean of the power estimate can then be filtered with an averaging infinite impulse response at step 258. In one embodiment, the average can include 50% old data and 50% new data. At step 260, the filtered average can be compared with a threshold. If desired, hysteresis can be employed in the threshold comparison. As a function of the comparison, the channel can selectively be muted (i.e., suppressed) at step 262. An indication that an artifact has been detected can be output to output module 124. This indication can then be relayed to the surgeon, for example through monitor 32. Thus, a false positive can be avoided and the surgeon is not erroneously alerted to EMG activity.

Figure 5:
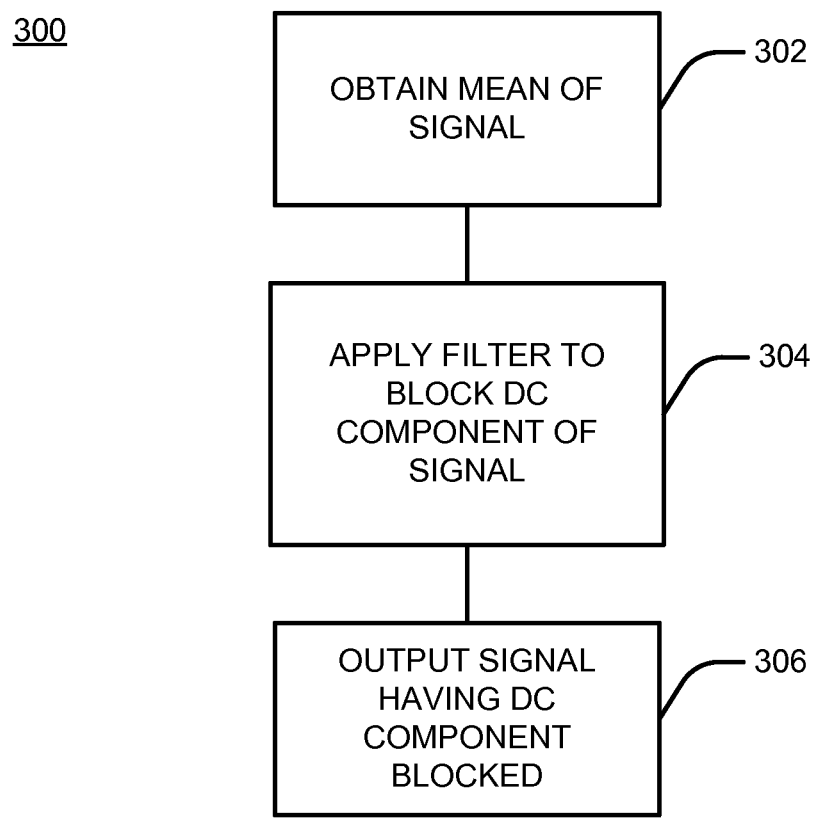
FIG. 5 is a flow diagram of a method for filtering a low frequency noise component from one or more channels that provide data to the nerve integrity monitoring system of FIG. 1.

FIG. 5 is a flow diagram of a method 300 for filtering a DC component from data input into the signal processing module 70. At step 302, the mean of the signal generated by method 200 (FIG. 3) is obtained. A low pass infinite impulse response filter is then used, at step 304, to filter a mean of the signal and block DC in the signal. One example filter uses the following equation:

$$y[n]=x[n]-x[n-1]+a \cdot y[n-1],$$

where x[n] is the input signal (received from input module 122), y[n] is the output signal and a is a constant. If desired, the value of a can be adjusted to block low frequency components of the signal as well. After application of the filter, the DC component of the signal is blocked. Then, the blocked DC signal is output at step 306.

Figure 6:
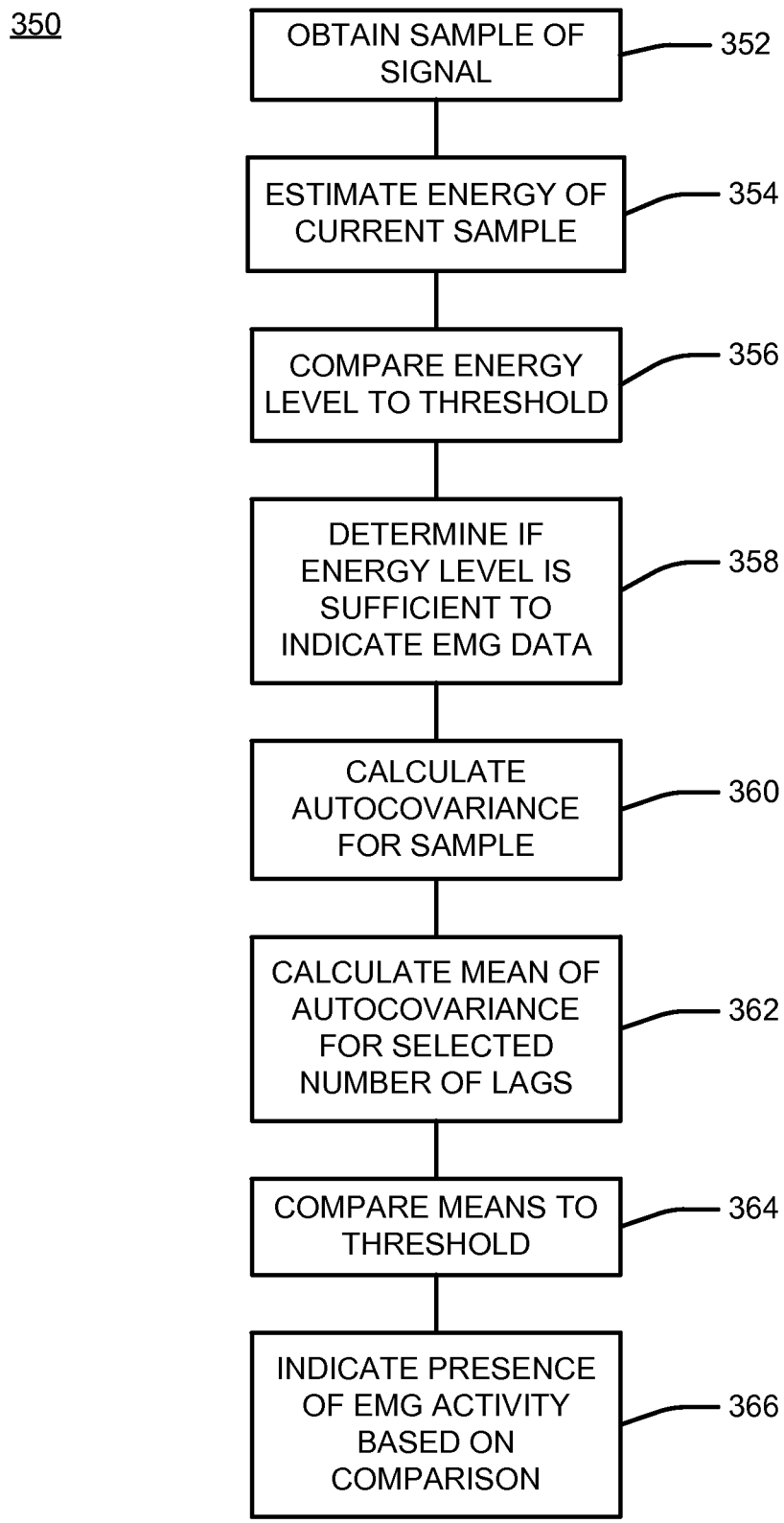
FIG. 6 is a flow diagram of a method for detecting EMG activity from one or more channels that provide input to the nerve integrity monitoring system of FIG. 1.

FIG. 6 is a flow diagram of a method utilized by EMG detection module 130 for detecting a level of EMG activity within a noisy environment, for example noise caused by an electrosurgical procedure. To detect a level of EMG activity, an autocovariance method is utilized to determine the presence of a high level of EMG activity. If a high level of EMG activity is detected during an electrosurgical procedure, the surgeon can be alerted. Method 350 begins at 352 where a sample of the signal is obtained from method 300 (FIG. 5). The energy of the sample is then estimated at step 354. The energy level is then compared to a threshold at step 356. Based on this comparison, a determination is made at step 358 as to whether the sample contains sufficient energy to indicate the presence of a high level of EMG activity. If a probe is poorly connected or has been disconnected from the patient tissue, the resulting signal will have limited energy and thus a low level of EMG activity will be provided to output module 124.

The autocovariance of the signal is calculated at step 360. As is known, the autocovariance is a coefficient that can be determined based on time-shifted observations of the signal as a function of a lag between observations. By analysis of EMG data, it has been determined that EMG data is highly correlated. Thus, highly correlated data can indicate a high level of EMG activity. At step 362, a mean for the autocovariance signal can be calculated for all or a selected number of lags. The calculated means are then compared to a threshold at step 364. If the means exceed the threshold, an indication of presence of a high level of EMG activity is provided at step 366.

Several adjustments can be made to method 350 to improve robustness. For example, a window function (e.g., a Bartlett window) can be applied to the samples obtained to reduce end effects that can be caused by calculating the autocovariance coefficients over a finite number of samples. Furthermore, a level detector can be utilized to determine if the signal is close to a rail (e.g., an upper or lower voltage level) of the ADC of input module 122. In this case, no EMG activity will be reported. Yet another adjustment can be made to the DC blocking filter. For example, the filter can be made more aggressive to attenuate low frequency data. Furthermore, multiple data buffers (e.g., four) can be used to improve the autocovariance results. If desired, the autocovariance calculation can be spread out the computing performance. Additionally, before comparing data to the EMG threshold, the mean of the square of selected coefficients can be used as a filter input to reduce noise and smooth data. It is worth noting that other methods of classification can also be used. For example, autocorrelation, wavelets, sigmoid functions, etc. can all be used to classify a noisy signal as containing EMG and/or detect EMG activity in a signal.

Figure 7:
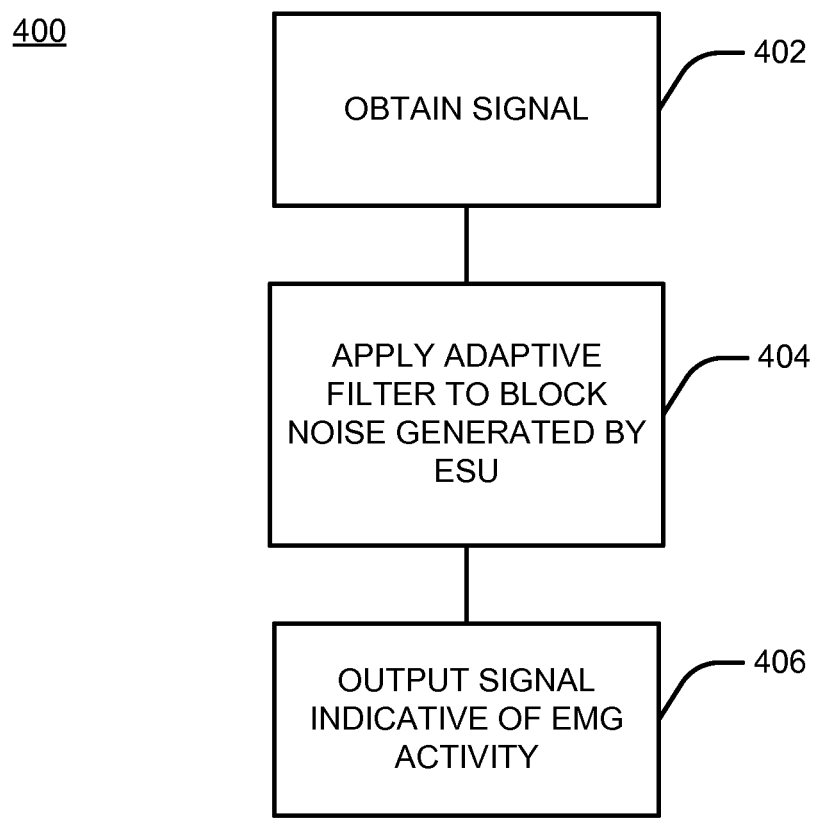
FIG. 7 is a flow diagram of a method for EMG signal recovery for one or more channels that provide data to the nerve integrity monitoring system of FIG. 1.

FIG. 7 is a flow diagram of a method 400 of applying an adaptive filter in an EMG recovery technique. Method 400 begins at step 402, where the input signal is obtained from the input module 122. At step 404, an adaptive filter is applied to the signal to block noise generated by the ESU 12. The filter can be reference based or non-reference based using various techniques. Once the noise generated by the ESU is filtered, a signal indicative of the EMG activity is output at step 406.

Various adaptive filters and adaptive filtering techniques can be employed in method 400. When using a reference based filter, one of the sensing probes 52 can be utilized to estimate the noise created by the electrosurgical unit 12 in the input signal. The data from the reference probe serves as the noise estimate to the adaptive filter. For example, a least mean square algorithm, a normalized least mean square algorithm, or a recursive algorithm can be used as a referenced based adaptive filter. These algorithms can be adjusted to vary a number of terms used and how data in the filter is processed to recover EMG data in a noisy signal created by electrosurgical unit 12.

Additionally, non-reference based adaptive algorithms can be used in method 400 to recover EMG data. Example filters include Kalman filters and H-infinity filters. These filters can also be adjusted as desired to produce a recovered EMG signal.

Although the present disclosure has been described with reference to preferred embodiments, workers skilled in the art will recognize that changes can be made in form and detail without departing from the spirit and scope of the present disclosure.

What is claimed is:

1. A surgical method, comprising:
    attaching a plurality of sensing probes to a tissue of a patient, the plurality of sensing probes electrically coupled to an input module;
    operating an electrosurgical unit proximate the plurality of sensing probes;
    simultaneously receiving first and second input signals from the plurality of sensing probes, the first input signal of the plurality of input signals indicative of electromyographic (EMG) activity of the patient and operation of the electrosurgical unit and the second input signal of the plurality of input signals indicative of an artifact of metal-to-metal contact;
    classifying the first input signal received from the plurality of sensing probes as a function of a level of EMG activity received from the patient with an EMG detection module; and
    providing an output signal indicative of the level of EMG activity with an output module;
    detecting for artifact in the second input signal with an artifact detection module; and
    providing a first indication to suppress the second input signal at the output module when artifact is detected in the second input signal.

2. The method of claim 1 wherein the artifact is detected based on an of power in the second input signal.

3. The method of claim 1 and further comprising:
    suppressing a direct current component or low frequency noise in the second input signal having a frequency lower than a threshold.

4. The method of claim 1 and further comprising:
    comparing a level of EMG activity in the plurality of input signals to a threshold and providing second indication of the comparison.

5. The method of claim 4 and further comprising:
    estimating a level of energy in the plurality of input signals to determine if the level of EMG activity is greater than an energy level threshold.

6. The method of claim 4 and further comprising:
    calculating an autocovariance or autocorrelation of the plurality of input signals to detect the level of EMG activity.

7. The method of claim 6 wherein the artifact is detected based on energy in the plurality of input signals and the autocovariance or autocorrelation.

8. The method of claim 5 and further comprising:
    classifying the plurality of input signals as EMG activity based on a wavelets or sigmoid classification function.

9. The method of claim 6 wherein calculating the autocovariance or autocorrelation of the plurality of input signals includes using multiple samples of the plurality of input signals.

10. The method of claim 1 and further comprising:
    filtering noise created by the electrosurgical unit and providing an EMG indication of EMG activity in the patient.

11. The method of claim 8 and further comprising:
    using a reference probe to estimate the noise created by the electrosurgical unit.

12. The method of claim 1 and further comprising:
    filtering a fundamental frequency of a noise signal generated by the electrosurgical unit.

\* \* \* \* \*